United States Patent
Liu et al.

(10) Patent No.: US 7,910,373 B2
(45) Date of Patent: Mar. 22, 2011

(54) $H_2O$ DOPED $WO_3$, ULTRA-FAST, HIGH-SENSITIVITY HYDROGEN SENSORS

(75) Inventors: Ping Liu, Denver, CO (US); C. Edwin Tracy, Golden, CO (US); J. Roland Pitts, Lakewood, CO (US); Se-Hee Lee, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 1533 days.

(21) Appl. No.: 10/240,082

(22) PCT Filed: May 5, 2001

(86) PCT No.: PCT/US01/14375
§ 371 (c)(1),
(2), (4) Date: Jan. 14, 2003

(87) PCT Pub. No.: WO01/86265
PCT Pub. Date: Nov. 15, 2001

(65) Prior Publication Data
US 2004/0023595 A1    Feb. 5, 2004

Related U.S. Application Data

(60) Provisional application No. 60/202,155, filed on May 5, 2000.

(51) Int. Cl.
*G01N 21/78* (2006.01)
(52) U.S. Cl. .................. 436/144; 422/86; 427/255.19; 436/154; 436/166
(58) Field of Classification Search .............. 422/86; 427/255.19; 436/144, 164, 166
See application file for complete search history.

(56) References Cited

U.S. PATENT DOCUMENTS

| | | | |
|---|---|---|---|
| 6,277,589 B1 * | 8/2001 | Seibert et al. | ............. 435/30 |
| 6,293,847 B1 | 9/2001 | Easter et al. | |
| 2004/0150867 A1 * | 8/2004 | Lee et al. | ............. 359/273 |

FOREIGN PATENT DOCUMENTS

| JP | 62257046 A | * 11/1987 |
|---|---|---|
| WO | WO 96/06203 | * 2/1996 |

OTHER PUBLICATIONS

Definition of "Resonse time": http://www.pc-education.mcmaster.ca/instrumentation/terminology.htm, Feb. 1, 2009.*
Definitions of "lag time" and "rise time": http://www.nwglde.org/glossary.html, Feb. 1, 2009.*
K. Ito and T. Ohgami, "Hydrogen detection based on coloration of anodic tungsten oxide film" Appl. Phys. Lett. vol. 60, Feb. 24, 1992, pp. 938-940.
Kim, D-J. et al., "A study on the hydrogen intercalation into rf-magnetron sputtered amorphous WO3 film using cyclic voltammetry combined with electrochemical quartz crystal microbalance technique" Solid State Ionics., North Holland Pub. Co. Amsterdam, NL, vol. 109, No. 1-2, Jun. 1, 1998, pp. 81-87.
Patent Abstracts of Japan, vol. 012, No. 136 (P-694), Apr. 26, 1988 & JP 62 257047 A(Hochiki Corp.), Nov. 9, 1987, abstract.
WO 96 06203 A (Optical Coating Laboratory Inc.) Feb. 29, 1996, p. 3, line 6, line 36, p. 11, line 13 and line 19.
Channin et al., "Display Devices", Springer-Verlag, 1980, 180-211.
Judeinstein et al., "Role of the Water Content on the Electrochromic Properties of WO3 nH20 Thin Films" Materials Science & Engineering, 1989, 129-132.

* cited by examiner

*Primary Examiner* — Jan M Ludlow
(74) *Attorney, Agent, or Firm* — Paul J. White

(57) ABSTRACT

An ultra-fast response, high sensitivity structure for optical detection of low concentrations of hydrogen gas, comprising: a substrate; a water-doped $WO_3$ layer coated on the substrate; and a palladium layer coated on the water-doped $WO_3$ layer.

8 Claims, 1 Drawing Sheet

H₂O DOPED WO₃, ULTRA-FAST, HIGH-SENSITIVITY HYDROGEN SENSORS

This application claims priority from U.S. Provisional Application Ser. No. 60/202,155, filed May 5, 2000.

CONTRACTUAL ORIGIN OF THE INVENTION

The United States Government has rights in this invention under Contract No. DE-AC36-99GO10337 between the United States Department of Energy and the National Renewable Energy Laboratory, a division of the Midwest Research Institute.

TECHNICAL FIELD

The invention relates to water doped tungsten oxide ($WO_3$—$nH_2O$) thin films for use in ultra-fast, high sensitivity gasochromic hydrogen sensors. The in-situ water-doped tungsten oxide is prepared during thermal evaporation of $WO_3$ on a glass substrate used as the chemochromic layer combined with a catalyst such as palladium, and utilized as an optical sensor to detect hydrogen.

BACKGROUND ART

Hydrogen is a plentiful, clean, non-polluting fuel. Hydrogen is currently used in many industries, and the US demand for hydrogen is approximately 140 billion cubic feet per year and growing. However, hydrogen is explosive at 4% in air. Therefore, it is critical to measure, monitor and control hydrogen wherever it is used.

In the gasochromic art where sensors and measurement instrumentation for hydrogen gases detect and/or measure hydrogen, typically there is required a portable sensing device, a kit (where hydrogen gas detection and/or measurement is required in existing equipment), and sensor heads installed at points where hydrogen leaks are possible, or where monitoring is necessary (i.e., in internal combustion engines which operate using hydrogen as a fuel).

The problems associated with current $H_2$ gasochromic devices is that these devices are not of adequate durability in that they degrade quickly with cycling and time, are too moisture sensitive, and react too slowly in response to the presence of $H_2$ to produce an optical absorption change with a lengthy real time constant in the vicinity of 30 seconds.

DISCLOSURE OF INVENTION

At present, $H_2$ detection is widely accomplished through the use of Pd/$WO_3$ hydrogen detecting gasochromic devices. However, several problems or drawbacks are associated with the use of Pd/$WO_3$ hydrogen detecting gasochromic devices. These problems are: 1) they are of inadequate durability; 2) they respond slowly to the presence of $H_2$; and 3) there is a conflicting cathodic-anodic optical response that results in a weakened color change.

The item 2) slow response of the Pd/$WO_3$ hydrogen detecting gasochromic device in the presence of a $H_2$ leak is due to the hydrogen reaction in $H_xWO_3$ which produces a slow optical absorption change within a lengthy room temperature time constant of about 30 seconds.

The slow response time of the Pd/$WO_3$ hydrogen detecting gasochromic device is exacerbated after storage of the sensor.

DISCLOSURE OF INVENTION

One object of the present invention is to provide a water doped $WO_3$/Pd thin film sensor structure for use in detecting the presence of hydrogen.

Another object of the present invention is to provide a water doped $WO_3$/Pd thin film structure for use in ultra-fast, high sensitivity hydrogen sensors.

A further object of the present invention is to provide water doped $WO_3$/Pd thin film sensor structures that provide faster response time to the detection of hydrogen than undoped $WO_3$/Pd.

In general, the invention is accomplished by providing a glass/W—$WO_3$/Pd sensor thin film structure, wherein, during deposition of the $WO_3$ layer upon glass by thermal evaporation, the $WO_3$ is doped with water by in-situ addition.

The in-situ addition results in improved hydrogen diffusion, and thus, improved response time. The in-situ addition also results in improved stability of the $WO_3$/Pd.

DETAILED DESCRIPTION OF INVENTION

Figure 1:
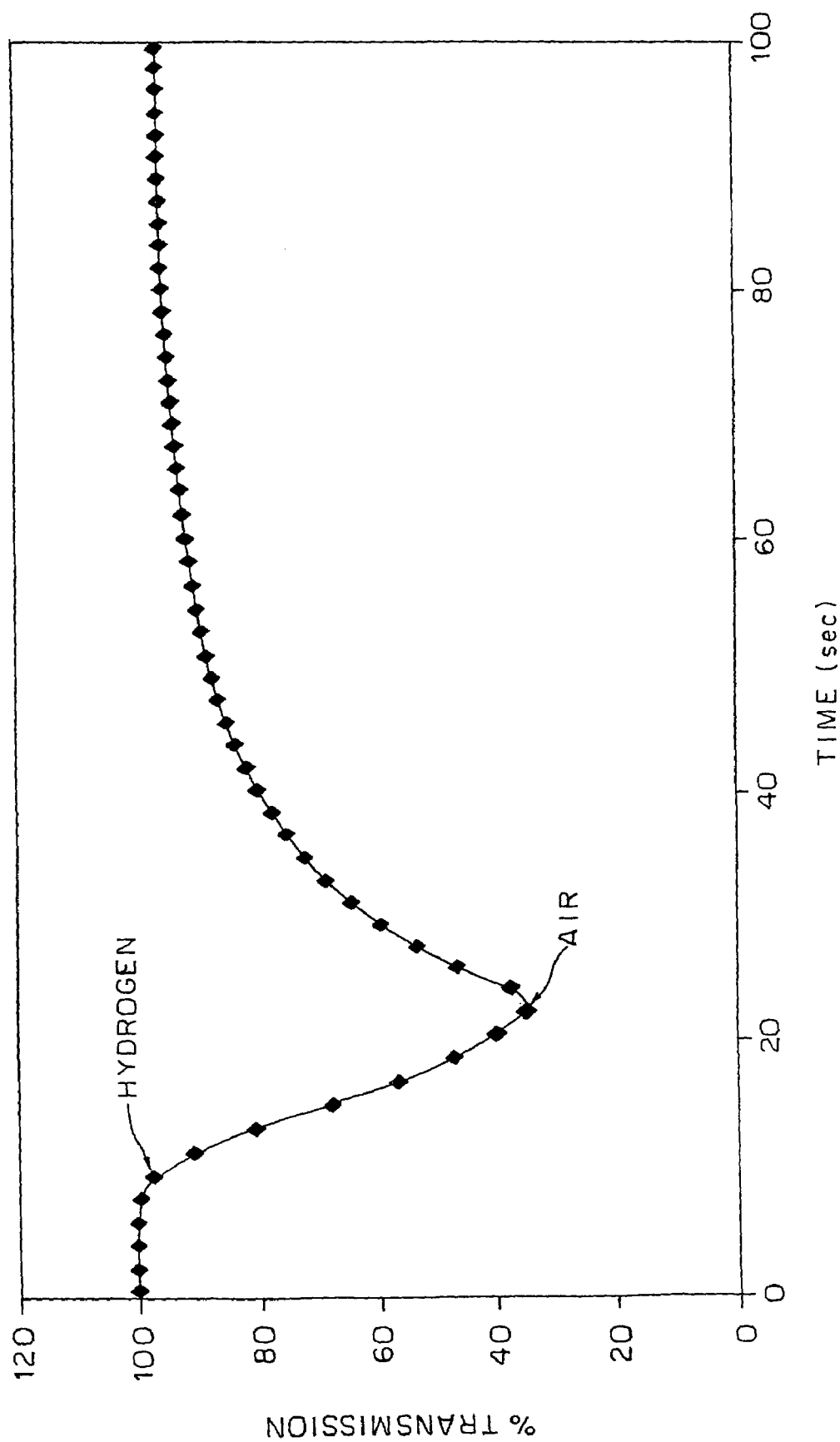
FIG. 1 is a graph showing percent relative transmission versus time for a water-doped $WO_3$/Pd sensor in a 1% hydrogen environment.

Due to the fact that Pd/$WO_3$ hydrogen sensors are encumbered by a slow response time, a need exists in the interest of safety to provide $H_2$ sensors of improved optical response time upon detecting hydrogen, which is explosive at 4% in air.

The Pd/$WO_3$ sensor is of slow response time because hydrogen reaction in $H_xWO_3$ produces optical absorption change with a room temperature time constant of about 30 seconds, as the rates of both hydrogen diffusion in the tungsten oxide layer and the charge transfer process at the palladium/tungsten oxide interface is slow.

The improved water-doped $WO_3$/Pd sensor of the invention is obtained by preferably depositing $WO_3$ on a glass substrate in a manner such that, during the deposition by thermal evaporation, the $WO_3$ is doped with water by in-situ addition.

During the in-situ addition of water to affect doping of the $WO_3$ layer, the water content in the film may be controlled by using different water vapor pressures during thermal evaporation.

The in-situ addition of water may also be accomplished by the use of other deposition processes such as plasma enhanced chemical vapor deposition (PECVD) and sputtering.

The slow response time of the Pd/$WO_3$ sensor upon detection of hydrogen, and the even slower response time of the Pd/$WO_3$ sensor upon detection of hydrogen after storage is significantly improved as a result of the invention process of providing in-situ, water-doped $WO_3$, during thermal evaporation deposition of the $WO_3$ layer onto a substrate.

The effect of water doping of the $WO_3$ layer is shown in TABLE I.

TABLE I

|  | Doped | Undoped |
|---|---|---|
| Full coloration time of fresh sensors | 1-2 s | ~30 s |
| Full coloration time after storage in ambient air for a week | 20 s | >600 s, unable to reach previous coloration |

As can be seen from TABLE I, the undoped $WO_3$ containing a sensor device requires approximately 30 seconds to achieve full coloration when the sensor is fresh or new. By contrast, the water-doped $WO_3$ containing a sensor device requires only 1 to 2 seconds for response time upon detection of hydrogen, and within this 1 to 2 seconds, full coloration of the sensor is attained.

In the case of storage of the undoped and doped sensors, after 1 week of storage of the sensor, full coloration of the undoped sensor could not be reached even after a period greater than 600 seconds. By contrast, the full coloration or reaction time after detection of hydrogen when the water-doped $WO_3$ containing sensor was stored for a week occurred in 20 seconds after detection of hydrogen.

The in-situ water doping of the tungsten oxide layer during deposition by thermal evaporation resulted in faster proton diffusion and resulted in an improved interface charge transfer rate at the interface between the water-doped $WO_3$/Pd layer.

Reference is now made to FIG. 1, which is a graph showing the percent transmission versus time for a water-doped $WO_3$/Pd sensor in a 1% hydrogen environment.

It is clear that the water-doped $WO_3$ containing sensor provides an extremely fast response upon detection of hydrogen and that the sensor is highly responsive to the presence of low-concentrations of $H_2$.

However, since the $WO_3$/Pd sensor becomes saturated at around the 2% level of hydrogen, the water-doped $WO_3$/Pd sensor may be used in combination with a vanadium oxide sensor to detect a full hydrogen concentration range above the 2% level.

The ultra-fast response to low concentrations of hydrogen gas as occasioned by the use of water-doped $WO_3$/Pd sensors is a result of faster proton diffusion and improved interface charge transfer rates. These technical improvements clearly provide a better margin of safety in environments where rapid detection of hydrogen leaks are decisive harbingers of eminent explosion.

The invention claimed is:

1. An in-situ water-doped Pd/$WO_3$, sensitivity sensor structure for full coloration optical detection of low concentrations of hydrogen gas at an ultra-fast response time within about 1-2 seconds compared to an undoped Pd/$WO_3$, sensor, comprising:
   a substrate;
   an in-situ addition of a water-doped $WO_3$—$nH_2O$) amorphous layer coated on said substrate by thermal evaporation; and
   a palladium layer coated on said water-doped $WO_3$—$nH_2O$-$nH_2O$ layer.

2. A method of preparing a water-doped —Pd/$WO_3$ high sensitivity sensor structure for optical detection of low concentrations of hydrogen gas at an ultra-fast response time compared to a Pd/$WO_3$ sensor, comprising:
   providing a substrate;
   depositing an amorphous layer of $WO_3$ upon said substrate by thermal evaporation while doping the $WO_3$ with water by in-situ addition; and
   depositing a layer of palladium onto the water-doped $WO_3$ layer.

3. An improved method of optically detecting low concentrations of hydrogen gas at an ultra-fast response time compared to an undoped Pd/Pd/$WO_3$ sensor comprising:
   subjecting a sensor comprising a substrate, a in-situ addition of a water-doped $WO_3$—$nH_2O$ amorphous layer coated on said substrate by thermal evaporation, and a palladium layer coated on said in-situ addition of water-doped Pd/$WO_3$—$nH_2O$ layer to an environment comprising hydrogen to obtain ultra fast full coloration of said sensor as a detection of hydrogen within about 1-2 seconds compared to an undoped Pd/$WO_3$ sensor.

4. The sensor structure of claim 1 wherein the amount of hydrogen in the environment is about 1%.

5. The sensor structure of claim 1 wherein said substrate is glass.

6. The method of claim 3 wherein the hydrogen environment is about 1%.

7. The method of claim 3 wherein said sensor structure is subjected to the hydrogen environment after storage in ambient air for about a week and full coloration on detection of hydrogen is about 20 seconds.

8. The method of claim 3 wherein said in situ addition of a water-doped Pd/$WO_3$ sensor is used in combination with a Pd/$WO_3$ sensor that becomes saturated at about 2% hydrogen levels.

* * * * *